United States Patent [19]

Bell et al.

[11] Patent Number: 5,597,733
[45] Date of Patent: Jan. 28, 1997

[54] AUTOMATIC MULTIPLE-SAMPLE MULTIPLE-REAGENT DISPENSING METHOD IN CHEMICAL ANALYZER

[75] Inventors: Charles A. Bell, Weston; Warren J. Heath, Marlboro; Norman M. Kleinman, Framingham, all of Mass.

[73] Assignee: Precision Systems, Inc., Natick, Mass.

[21] Appl. No.: 404,168

[22] Filed: Mar. 14, 1995

Related U.S. Application Data

[63] Continuation of Ser. No. 93,576, Jul. 19, 1993, abandoned, which is a continuation-in-part of Ser. No. 807,772, Dec. 9, 1991, Pat. No. 5,229,074, which is a continuation of Ser. No. 224,059, Jul. 25, 1988, abandoned.

[51] Int. Cl.$^6$ .................................................. G01N 35/10
[52] U.S. Cl. .......................... 436/54; 422/63; 422/67; 422/100; 436/43; 436/47; 436/49; 436/180; 73/864.21
[58] Field of Search .................................. 436/43, 47, 49, 436/50, 54, 55, 174, 179, 180, 807; 422/63, 64, 65, 67, 100; 73/864.21; 141/1, 2, 130

[56] References Cited

U.S. PATENT DOCUMENTS

| | | | |
|---|---|---|---|
| 3,192,968 | 7/1965 | Baruch et al. | 422/64 |
| 3,767,364 | 10/1973 | Ritchie et al. | 422/50 |
| 3,801,283 | 4/1974 | Shapiro et al. | 422/64 |
| 3,912,456 | 10/1975 | Young | 436/47 |
| 4,076,503 | 2/1978 | Atwood et al. | 422/100 |
| 4,154,795 | 5/1979 | Thorne | 422/99 |
| 4,215,092 | 7/1980 | Suovaniemi et al. | 422/100 |
| 4,276,051 | 6/1981 | Ginsberg et al. | 422/63 |
| 4,311,667 | 1/1982 | Gocho | 422/64 |
| 4,326,851 | 4/1982 | Bello | 422/63 |
| 4,344,768 | 8/1982 | Parker et al. | 422/64 |
| 4,357,301 | 11/1982 | Cassaday et al. | 422/64 |
| 4,429,583 | 2/1984 | Watanabe et al. | 73/864.12 |
| 4,456,037 | 6/1984 | Gocho | 141/1 |
| 4,639,135 | 1/1987 | Borer et al. | 356/246 |
| 4,675,162 | 6/1987 | Sakamaki et al. | 422/65 |
| 4,774,055 | 9/1988 | Wabatake et al. | 422/64 |
| 4,888,998 | 12/1989 | Buzza et al. | 73/864.21 |
| 4,905,526 | 3/1990 | Magnussen, Jr. et al. | 73/864.18 |
| 4,906,433 | 3/1990 | Minekane | 422/67 |
| 4,933,147 | 6/1990 | Hollar et al. | 422/102 |
| 5,051,238 | 9/1991 | Umetsu et al. | 422/64 |
| 5,215,714 | 6/1993 | Okada et al. | 422/64 |

FOREIGN PATENT DOCUMENTS

| | | |
|---|---|---|
| 0041378 | 12/1981 | European Pat. Off. . |
| 0217000 | 4/1987 | European Pat. Off. . |
| 3343176 | 6/1984 | Germany . |
| 2121169 | 12/1983 | United Kingdom . |

OTHER PUBLICATIONS

"COBAS MIRA™ the mini random access system," Roche Diagnostic Systems brochure, 1985.

(List continued on next page.)

*Primary Examiner*—Long V. Le
*Attorney, Agent, or Firm*—Hamilton, Brook, Smith & Reynolds, P.C.

[57] ABSTRACT

An analyzer for chemical assays includes a turntable which supports sample containers and reagent containers within a cooled volume and test cells about the periphery of the cooled volume. A probe is carried by a rotating arm for withdrawing liquid from the containers and dispensing the liquid. Fixed stations are also provided in the path of the probe. One such station serves to both wash the tip of the probe and to receive samples for flow-through analysis. Heaters associated with the probe and with the test cells increase the rate of reaction. Curved walls of test cell segments match the optics of an optical analyzer so that light from the analyzer lamp is generally orthogonal to the curved surfaces. The light voltage of the lamp may be controlled as a function of lamp wavelength required for particular assays. The system provides multiple-point calibration and automatic dilution of samples. Multiple aliquots of reagent may be drawn into the probe and then be dispensed into separate test cells. Individual aliquots of sample may be drawn and dispensed with the reagent.

2 Claims, 8 Drawing Sheets

OTHER PUBLICATIONS

Alpert, Nelson L., ed., "COBAS MIRA™", *Clinical Instrument Systems,* vol. 7, No. 2, Feb. 1986, pp. 1–8.

"Gem Profiler™" the 8–minute random access chemistry profile, Electro–Nucleonics, Inc., brochure.

"Clinical chemistry analyzer," *Clinical Lab Products,* vol. 10, No. 12, Dec. 1981.

"The Abbott Commander Sample Management Center," Abbott laboratories brochure, 1986.

"Encore™ System II," Baker Instruments brochure, Oct. 1984.

Suarez, Ricardo E. et al., "All–MOS charge redistribution analog–to–digital conversion techniques—Part II", *Journal of Solid–State Circuits,* vol. SC–10, No. 6, Dec. 1975, pp. 379–385.

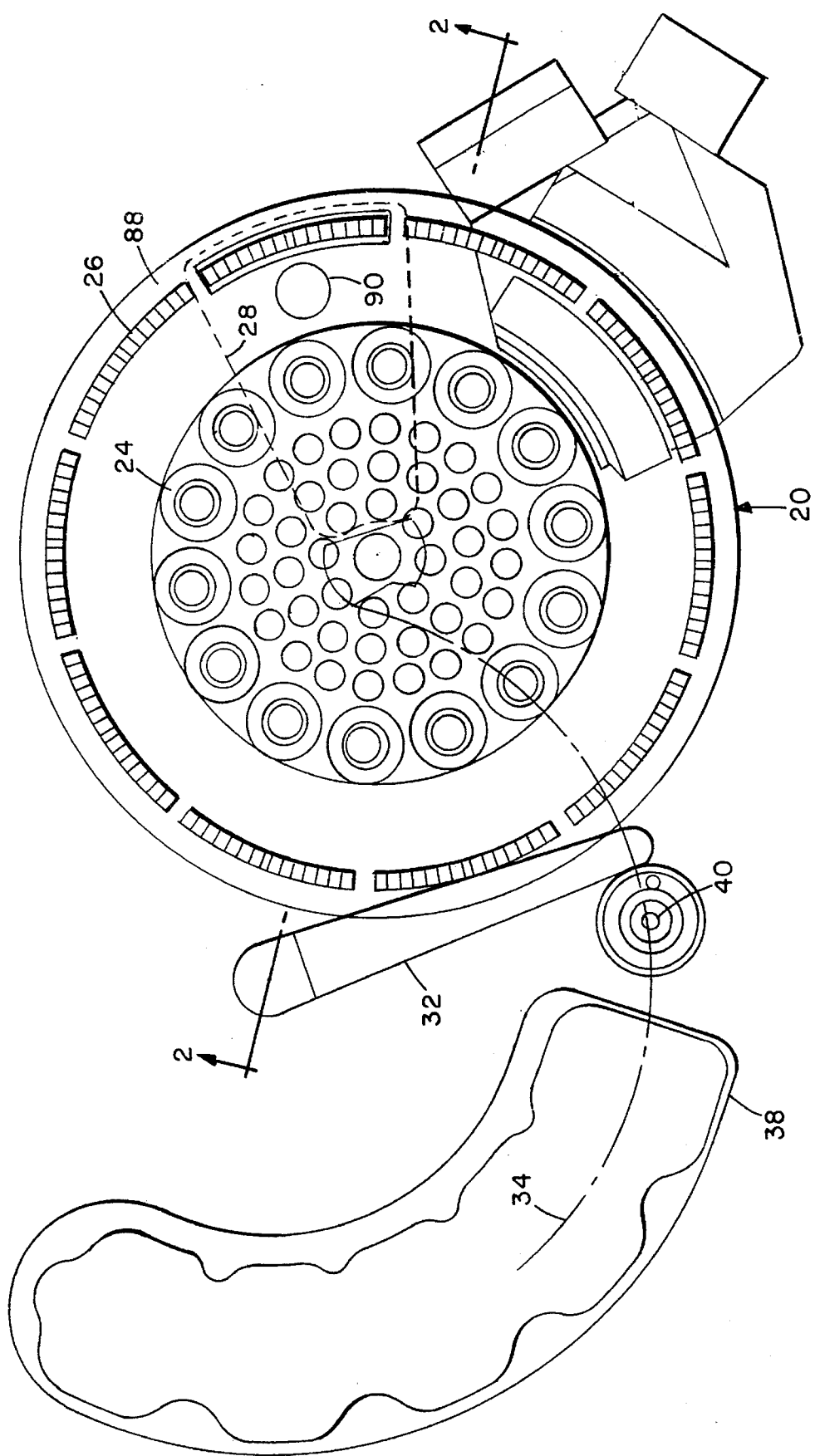
FIG. I

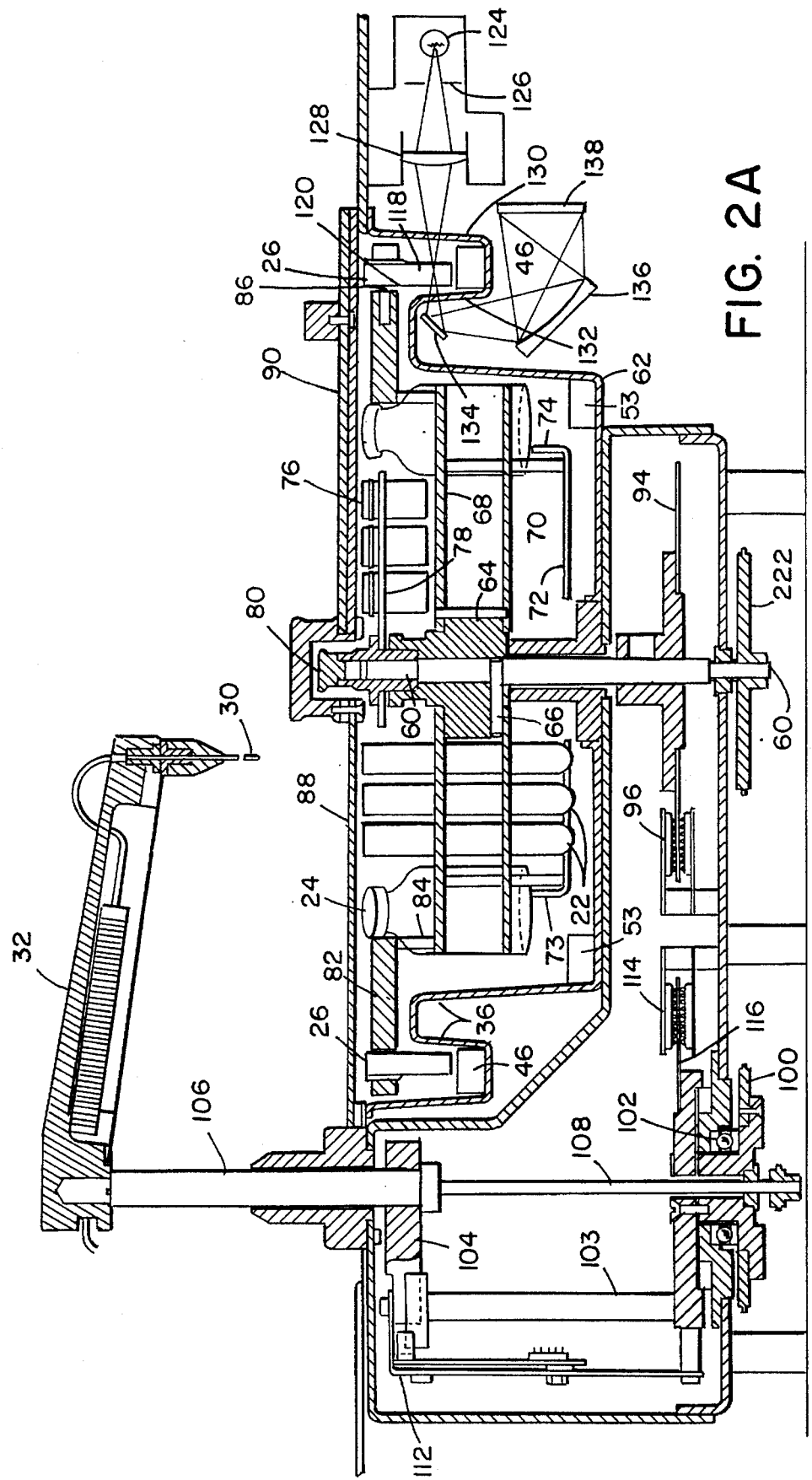

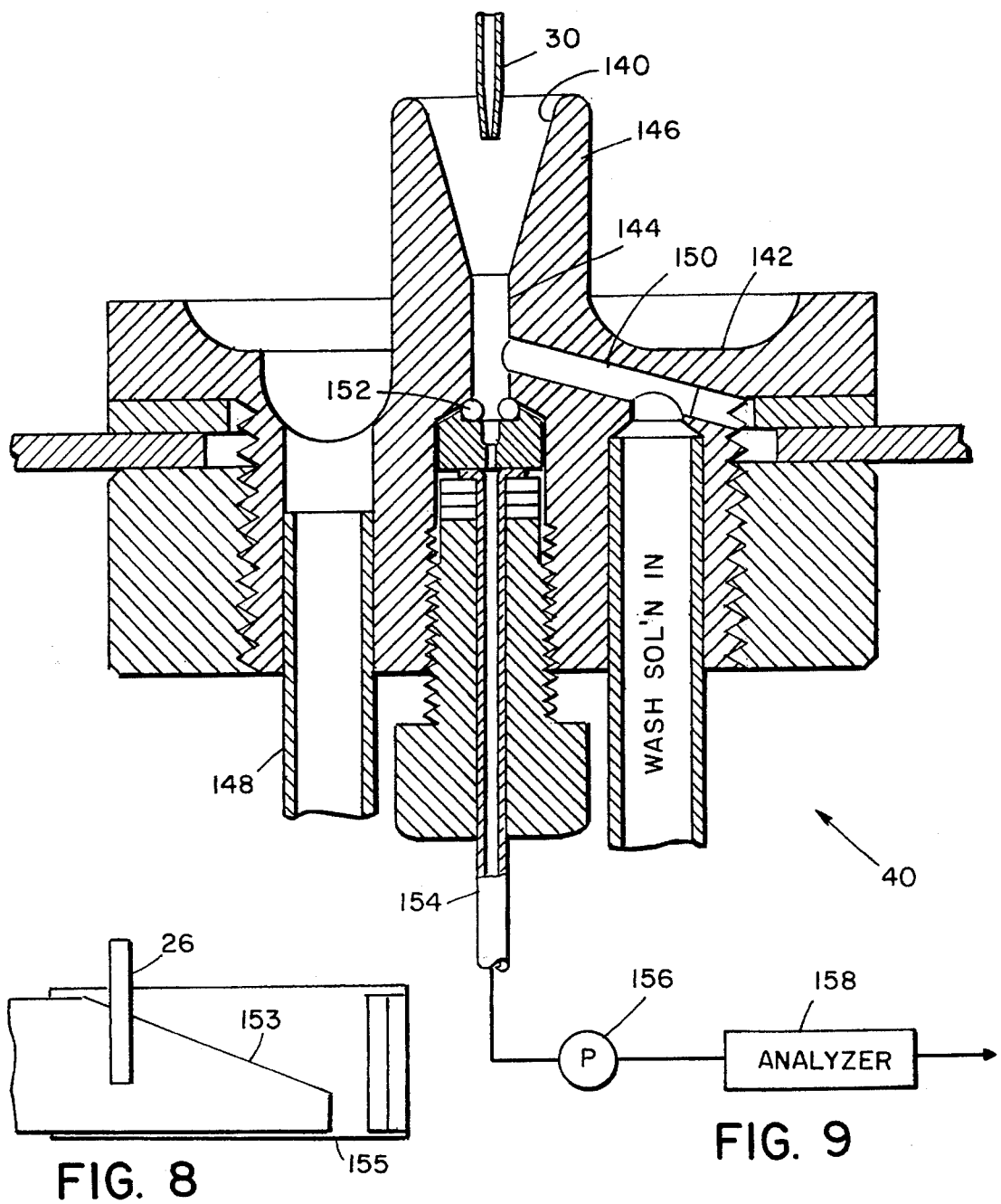
FIG. 8
FIG. 9
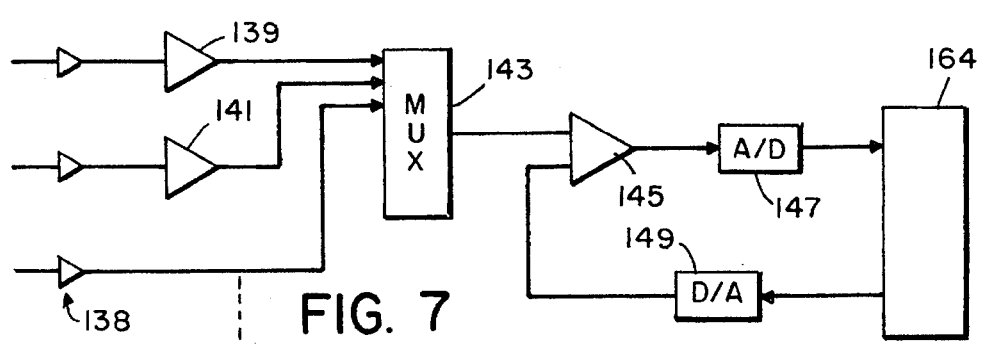
FIG. 7

AUTOMATIC MULTIPLE-SAMPLE MULTIPLE-REAGENT DISPENSING METHOD IN CHEMICAL ANALYZER

RELATED APPLICATIONS

This application is a continuation of Ser. No. 08/093,576, filed Jul. 19, 1993, now abandoned, which is a continuation-in-part application of U.S. Ser. No. 07/807,772, filed Dec. 9, 1991, now U.S. Pat. No. 5,229,074, which is a File Wrapper Continuation of U.S. Ser. No. 07/224,059, filed Jul. 25, 1988, now abandoned. All of the above applications are incorporated herein by reference in their entirety.

BACKGROUND OF THE INVENTION

Chemical assays, particularly biochemical assays, must often be performed on a large number of samples taken from test tubes or other sample containers. Further, it is often necessary to perform different assays on each of the many samples, each assay requiring mixing of one or more reagents with a sample and performing an analysis such as an optical analysis. Performing such multiple assays on multiple samples manually is very time consuming and subject to error. More recently, robotic systems have been developed to automatically withdraw sample liquid from sample containers and reagent from reagent containers and to mix the two in test cells for analysis. The sample containers and test cells may be positioned in circular arrays on turntables. One or more probes on arms carry sample liquid to the test cells and reagent from reagent containers to the test cell.

DISCLOSURE OF THE INVENTION

The present invention relates to improvements to automatic analyzers.

In one form of the invention, a turntable removably supports a plurality of sample containers and a plurality of larger reagent containers in a circular array. A peripheral array of transparent test cells is also supported on the turntable. An optical analyzer is positioned to illuminate selected test cells and detect light from the cells. A translatable probe is able to withdraw liquid from selected ones of the sample and reagent containers and dispense the withdrawn liquid into a selected test cell. The probe is selectively positionable over all sample and reagent containers and all test cells with translation of the probe and rotation of the turntable.

Preferably, a cooler cools the sample and reagent containers supported on the turntable in order to extend the useful life of each. The test cells are grouped as segments which surround, but are thermally isolated from, the sample and reagent containers. A heater is provided to heat the liquid drawn into the probe before the liquid is dispensed from the probe. Further, a heater may be provided to heat test cells. The heating increases the rate of reaction and insures that all readings are performed at an appropriate temperature.

Preferably, the probe is positioned on the end of a rotating arm which is also mounted for vertical translation. A detector may be provided for detecting the vertical height of the probe, and a level detector may be provided for detecting the position of the probe relative to liquid within a container. The level of liquid in all of the containers may thus be monitored and the amount of immersion of the probe may be controlled. Optical encoders may accurately indicate the angular position of each of the turntable and the rotating arm and the height of the arm.

A plurality of fixed stations, which need not be cooled with the samples and reagents on the turntable, may also be positioned along the path of the probe but away from the turntable. Preferably, one of the fixed stations is a probe washer. The probe washer comprises a well into which the probe may be positioned and a fluid inlet for introducing washer fluid into the well. The washer further includes a conduit at the base of the well into which the tip of the probe may be positioned. The conduit is coupled to a flow-through analyzer so that, after washing of the end of the probe, the probe may be positioned to inject liquid therefrom to the flow-through analyzer.

The turntable may include a first tray adapted to carry elongated sample containers and the reagent containers and a second tray positionable over and removable from the first tray and coupled to rotate therewith. The second tray is adapted to carry shorter sample containers.

Preferably, the test cells comprise inner and outer transparent walls which are curved along inner and outer surfaces. The curved surfaces minimize reflections and chromatic aberrations and thus permit the use of a lamp and lens system having a lower F number of less than 5. A lower power lamp may thus be used. The test cells may be formed in circular segments of multiple cells. Each circular segment comprises inner and outer curved walls joined by cell dividing walls. A notch may be provided in the bottom of each segment so that the segment can be dispensed along a narrow ramp into a drawer for disposal after use.

The level of electrical output to a lamp which illuminates the test cell may be controlled as a function of wavelength of interest in an optical analysis. This level control extends the life of the lamp where high electrical input must be provided to obtain light of particular wavelengths but those wavelengths are not always required. The analyzer may include a grating which receives light from the test cell and directs different wavelengths of light to different portions of a detector array.

Mixing of sample liquid and reagent introduced into a test cell may be obtained by short, relative movement between the probe and the turntable when the probe is inserted into a test cell. Movement may be obtained by oscillating the probe drive and/or the turntable drive.

Preferably, the controller is responsive to bar code input identifying samples and bar code inputs which determine particular assay procedures for the samples. Those procedures may include a calibration cycle in which optical analyses of standard samples from plural, predetermined containers on the turntable are performed to define a calibration curve. Thereafter, the calibration curve may be used to calibrate tests of samples from other sample containers. Preferably, any dilution of the samples is also performed automatically with the system providing an analysis output as a function of the amount of dilution. The dilution may be performed automatically where analysis output levels are found to be above a highest calibration level, or the dilution may be performed in response to operator instructions.

The analyzer may include a number of motors, each having plural coils. A single set of drivers may be coupled to the coils of all of the motors, and selective drivers, each associated with a motor, select one motor at a time. Each selective driver may be coupled in common with all coils of its motor. The motors are mounted with shock absorbing couplings.

Output from a detector array may be multiplexed and amplified. The amplifier output is applied through an analogto-digital converter to a computer. Through a digital-to-analog converter, the computer adjusts the gain of the amplifier to provide an output within the range of the analog-to-digital converter.

BRIEF DESCRIPTION OF THE DRAWINGS

The foregoing and other objects, features and advantages of the invention will be apparent from the following more particular description of a preferred embodiment of the invention, as illustrated in the accompanying drawings in which like reference characters refer to the same parts throughout the different views. The drawings are not necessarily to scale, emphasis instead being placed upon illustrating the principles of the invention.

FIG. 1 is a plan view of an analyzer embodying the present invention.

FIG. 2A is a partial sectional view of the system of FIG. 1 taken along the lines 2—2, with the arm rotated.

FIG. 7 is an illustration of light detector circuitry.

FIG. 8 is a schematic illustration of a ramp and drawer for dispensing used test cell segments.

FIG. 9 is a sectional view of the washer/injector station of FIG. 1.

FIGS. 11A and 11B illustrate two sides of a sheet for bar code input of assays to be performed.

DESCRIPTION OF A PREFERRED EMBODIMENT

Figure 2B:
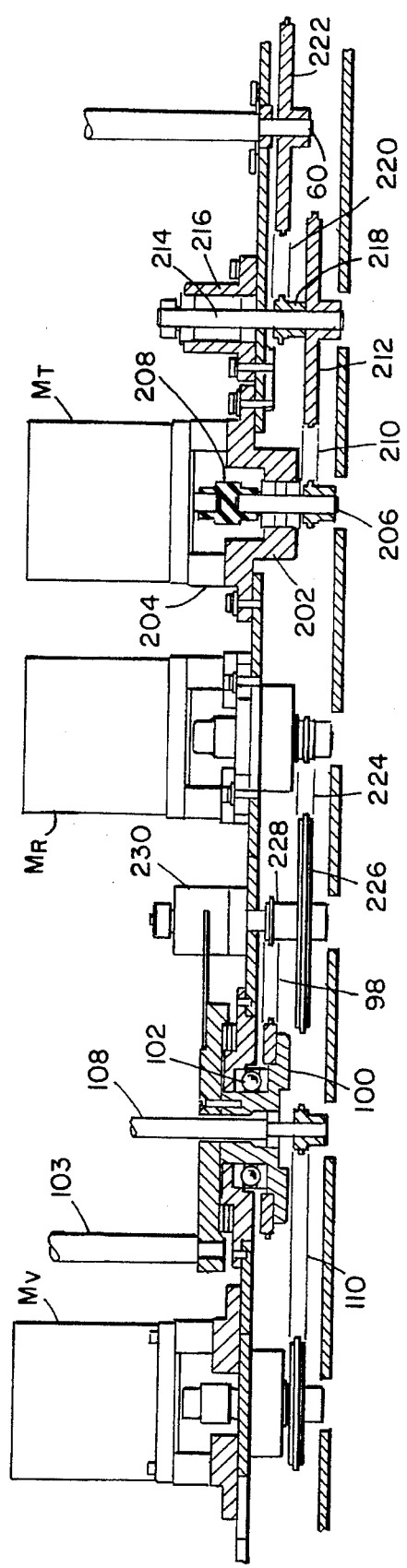
FIG. 2B is a side view of the turntable and arm drive mechanism.

A plan view of an analyzer embodying the present invention is illustrated in FIG. 1. The analyzer includes a turntable 20 which carries a circular array of 42 sample containers 22 and 14 larger reagent containers 24 which surround the sample containers. Ten test cell segments 26, each having fourteen test cells formed therein, surround the reagent containers. As illustrated in FIG. 2A, a probe 30 extends below a rotating arm 32. As illustrated in FIG. 1, the arm 32 may be rotated to position the probe 30 over any one of the sample and reagent containers and test cells by rotation of the arms and rotation of the turntable. The arm 32 is then translatable vertically to position the tip of the probe 30 within the selected container or test cell and withdraw or dispense liquid. The probe follows a curved path 34.

As illustrated in FIG. 2A, the sample and reagent containers are isolated from the test cells by a wall 36. This wall allows the inner containers to be cooled 53 by air flow from a Peltier cooler, to extend the useful life of the samples and reagents while permitting the mixed sample and reagent in the test cells to be held at a higher temperature to increase the rate of reaction. Some reagents and other solutions should not be refrigerated. Thus, a curved tray 38 is provided for containers of such liquids (FIG. 1). The tray positions the containers along the path 34 of the probe.

In usual procedures, the probe is washed after a sample or reagent is drawn into the probe to remove the sample or reagent from the sides of the probe. Because this washing procedure is performed often, a washing station 40 is positioned close to the turntable along the path 34. In a typical procedure, 350 milliliters of reagent might be pulled from a reagent container 24 with the probe 30. The probe would then be positioned over and dipped into the washer station to clean reagent from the sides of the probe. Then the reagent might be drawn into the probe even further to create an air pocket before positioning the probe in a sample container to draw sample into the probe. Again, the probe would be washed at the station 40. The probe would then be positioned over a test cell, and the sample and reagent would be dispensed into the test cell. The precise time at which the sample and reagent are dispensed into the test cell would be noted by a controller, and the reaction would be allowed for some predetermined time before performance of an optical analysis. Injecting the liquids into the test cell may provide sufficient mixing. If not, mixing may be performed by positioning the probe in the test cell and causing short oscillations of the probe or the turntable or both by means of their principal drive motors. Because of the curved paths of the probe and test cells, driving both together results in an elliptical stirring movement of the probe.

Figure 3:
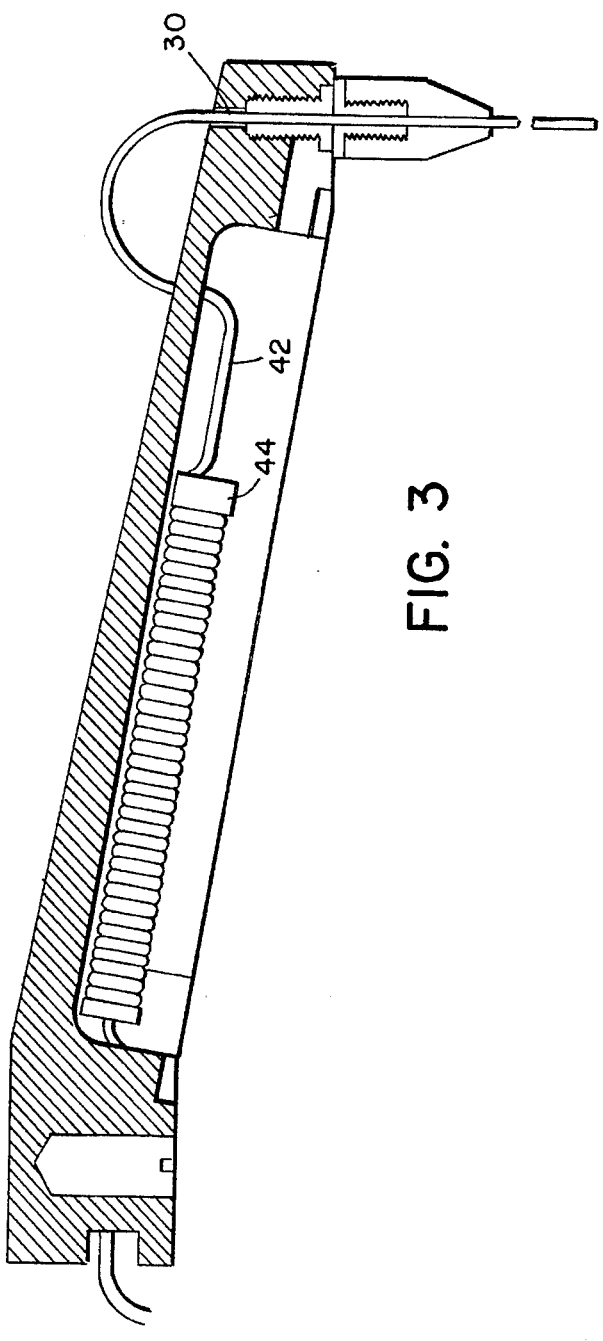
FIG. 3 is a view of the probe arm of FIGS. 1 and 2 partially broken away and enlarged.

As illustrated in FIG. 3, tubing 42 from the upper end of the probe 30 is wrapped around a heating unit 44. Thus, liquid drawn into the probe may be warmed to proper reaction temperature before being dispensed into the test cell. As a result, the heater 46 (FIG. 2A) positioned below the test cells at the optical analyzer need not have a large heating capacity.

Figure 4:
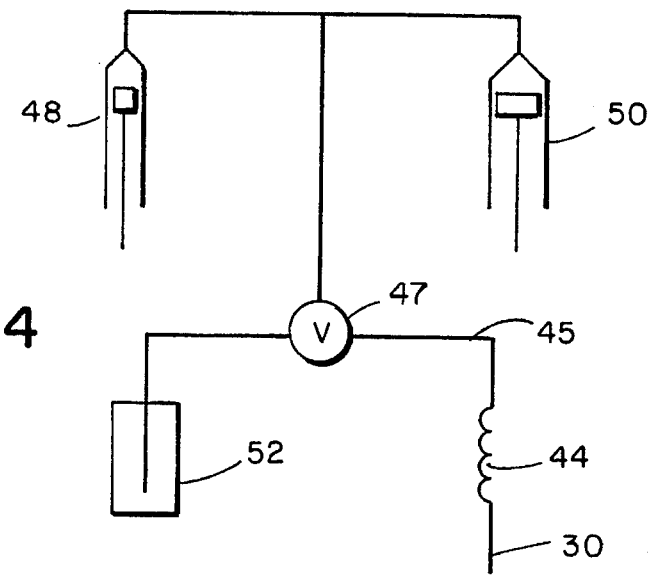
FIG. 4 is a schematic illustration of the probe and associated valve and heater pumps.

As illustrated in FIG. 4, liquid is drawn into the probe and about the heater 44 through a tube 45 and valve 47 by one of two reciprocal pumps 48 and 50. The pumps are of different cross-sectional areas in order to precisely draw small amounts of liquid or less precisely draw larger amounts of liquid. The two-way spool valve 47 allows buffer solution to be drawn from a reservoir 52 into the pumps to prime the pumps. Further, in some cases it might be desirable to dispense buffer solution from the reservoir 52 into a test cell. For example, the system may automatically dispense a measured amount of buffer solution into a test cell with a sample to dilute the sample. By diluting samples automatically rather than before placement of a sample into the system, errors in computing the results of an analysis as a function of dilution may be minimized. Also, where the system detects an output from an analysis which is above a calibration level of the system, the system may automatically dilute the sample and provide accurate measurements from the diluted sample. Additional pumps and sources of solution may also be provided.

Further details of the turntable and drive mechanism are illustrated in FIGS. 2A and 2B.

The turntable is removably positioned over a drive shaft 60 which extends through the base of a turntable well 62. The turntable includes a center hub 64 which drops down over the shaft 60 and is keyed thereto by pin 66 carried by the shaft 60. Disks 68 and 70 are mounted to the hub 64 and have holes therein dimensioned to receive conventional test tube sample containers. Test tubes 22 are supported by a lower carrier disk 72 which is carried by the discs 68 and 70 through struts 73. An upwardly directed flange 74 supports the reagent containers 24 which are positioned in larger peripheral holes about the disks 68 and 70. As illustrated, the reagent containers may be tilted to facilitate withdrawal of reagent when the reagent level is low.

Test tubes 22 are shown positioned in the turntable to the left of the shaft 60 (FIG. 2); to the right of the shaft, a partially shown optional tray for smaller sample containers 76 is positioned on the hub 64. The tray for smaller containers includes a disk 78 having holes therein for the containers. The disk is carried by a center hub 80 which may be dropped onto the upper end of the hub 64.

The test cell segments 26 are carried by an outer ring 82 which is coupled to the disk 68 by struts 84. The test cell segments are retained within curved slots in the ring 82 by bullet detents 86.

The entire turntable well may be covered by a cover plate 88 illustrated in FIG. 2. That cover plate has an opening shown by broken lines 28 in FIG. 1 which may be closed by hinged closure 90. With the cover plate on and closed, the sample and reagent containers can be kept cool. The closure 90 may be opened for selective replacement of test cell segments and sample and reagent containers, and the full plate 88 may be removed to replace an entire turntable or small sample container tray.

An optical encoder disk 94 fixed to the shaft 60 and a set of LEDs and detectors 96 may be used to provide precise indications of the position of the turntable to the main controller.

The arm 32 may be rotated by a belt 98 which rotates a lower hub 100 about bearings 102. The hub 100 carries a vertical guide post 102 which rides in a hole in a plate 104. The plate 104 is fixed to the arm support shaft 106 and thus rotates the arm 32 with rotation of the plate 100 and post 102.

The height of the arm 32 is adjusted by means of a screw 108 which extends through the bearing 102 and plate 100 into the shaft 106. With rotation of the screw 108 by a belt 110, the shaft and the rotor plate 104 may be translated up or down. The plate 104 is detected at its highest point by a detector 112. The angular position of the arm 32 throughout rotation may be detected by a set of LEDs and detectors 114 which view an optical encoder 116.

The drive system of an analyzer needs to be simple to assembly, easy to manufacture, easy to repair, and provide little addition to the noise of the analyzer, since it is used in environments which may find excess instrument noise objectionable. The avoidance of complicated machined parts and castings is also desirable.

FIG. 2B illustrates the drive to the turntable and probe arm. Three stepper motors $M_T$, $M_R$, and $M_V$ drive the turntable, rotate the arm, and vertically drive the arm. Each is coupled to the system through shock absorbers. For example, the motor $M_T$ is coupled to a mounting 202 through a set of four shock absorbing isolators 204. Also, the motor drives a shaft 206 through a rubber coupling 208. The shaft 206 drives a belt 210 which drives a wheel 212 mounted on a shaft 214 carried by a bearing 216. The shaft 214 also carries a wheel 218 which drives a second belt 220. The belt 220 drives a wheel 222 to drive the shaft 60 of the turntable. The several wheels and belts provide for a desired gear ratio in the drive.

Similarly, the motor $M_R$ drives the lower hub 100 of the rotating arm through belts 224 and 98 and the wheels 226 and 228 carried by the bearing 230. The screw 108 is driven directly by the motor $M_V$ through belt 110.

Figure 5:
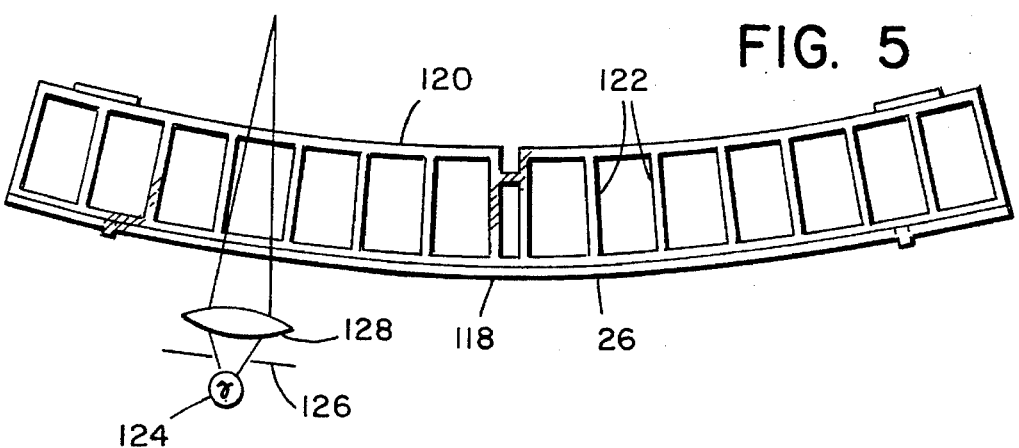
FIG. 5 is a plan view of a test cell segment in the system of FIG. 1.
Figure 6:
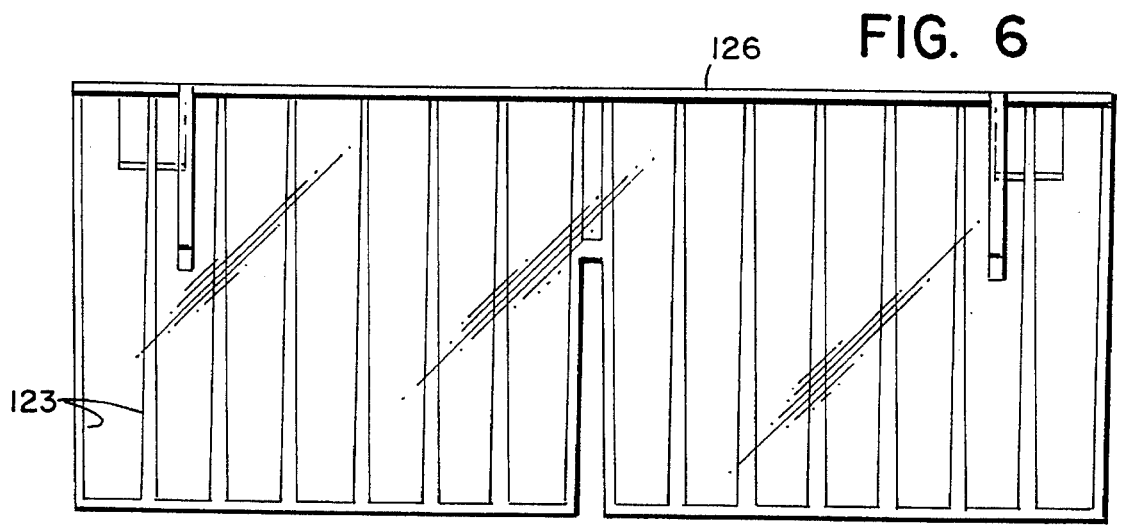
FIG. 6 is an unwrapped side view of the test cell segment of FIG. 4.

FIGS. 5 and 6 illustrate a test cell segment 26. The segment comprises outer and inner walls 118 and 120 joined by dividing walls 122 which define individual test cells. The walls 118 and 120 are frosted at 123 along the inner dividers to a height corresponding to the analyzer light path in order to intercept light which might pass through the divider walls and interfere with measurements. The bottom of the segment is also transparent to allow for fluorescence analysis. By forming the cells with shared dividing walls 122, the number of cells which can be obtained about a given circumference can be maximized, the amount of plastic used is reduced and the mold is simplified.

As described above, the turntable can be rotated to move a selected test cell into an optical analyzer station illustrated schematically in FIG. 2A. At the analyzer, light from a lamp 124 is directed through an aperture 126 and lens system 128 toward the test cell. The light passes through holes in the walls 130 and 132 in the well 62 and through the transparent front and rear walls 118 and 120 of the test cell. The light is reflected by a mirror 134 to a concave holographic grating 136. The grating separates the light according to wavelength and distributes the separated light along a detector array 138. Thus, the absorption of light from the lamp 124 by the liquid in the test cell may be determined as a function of wavelength. Trichromatic or polychromatic corrections are readily implemented with the data obtained from the array of detectors.

The detector circuitry is illustrated in FIG. 7. Signals from the individual diodes of the array 138 may be selectively amplified by preamplifiers such as 139 and 141. Where the signal is known to be sufficiently large, preamplification is not required. All of the signals from the diodes are multiplexed by a multiplexer 143 to the input of a log amplifier 145. The output of the amplifier 145 is converted to a digital signal by means of an analog-to-digital converter 147 and applied to a local process controller 164. The controller 164 returns a signal through a digital-to-analog converter 149 to adjust the gain of the log amplifier 145. Using an inexpensive 4-bit digital-to-analog 149, the output of the log amplifier can be held within the range of an inexpensive analog-to-digital converter 147.

As illustrated in FIG. 5, both inner and outer surfaces of the front and back walls 118 and 120 are curved. This curve minimizes reflections and aberrations and thus enables the use of an illuminating system having a low F number of less than 5. Prior systems have used test cells with flat walls and have required illumination systems of a high F number to avoid aberrations. The high F number in turn required the use of high-power lamps.

As illustrated in FIG. 6, the test cell segment has a central notch 151 formed in its base. This notch facilitates dispensing of used segments from the analyzer. As illustrated in FIG. 8, a ramp 153, which is sufficiently narrow to be received within the notch 15, is provided below the opening 28 (FIG. 1) in the turntable cover. After a test cell has been used, it may be dispensed by pressing a new test cell segment against the used segment to press it down onto the ramp 153. The ramp 153 guides the segment into a drawer 155 previously positioned in the analyzer housing. The drawer has an opening in the rear to receive the ramp 153 and is disposable with the used test cell segments.

FIG. 9 illustrates the novel washer station 40. Washer stations typically include a center well surrounded by a basin 142. Wash liquid is directed upwardly from an inlet 144 in the base of the well, past the probe 30 to clean the outer walls of the probe and over the wall 146 of the well into the basin 142. From the basin, the waste wash liquid is drained through a conduit 148.

In the present system, the wash solution is introduced through a side port 150. Below the port 150, an o-ring 152 is provided for receiving and sealing about the end of the probe. The o-ring 152 is at the mouth of an injection station conduit which leads through a pump 156 to a flow-through analyzer 158. It is usual to first wash a probe prior to moving the probe to an injection station. The combination washer/injector of FIG. 6 provides both functions at a single station. The probe is washed as it is lowered into the injection station. The flow-through analyzer may be of any known type and many different analyzers may be provided. Known flow-through analyzers include those used for pH and, Other ion detection, $CO_2$ and $O_2$. Further, the analyzer might be an optical analyzer.

Figure 10:
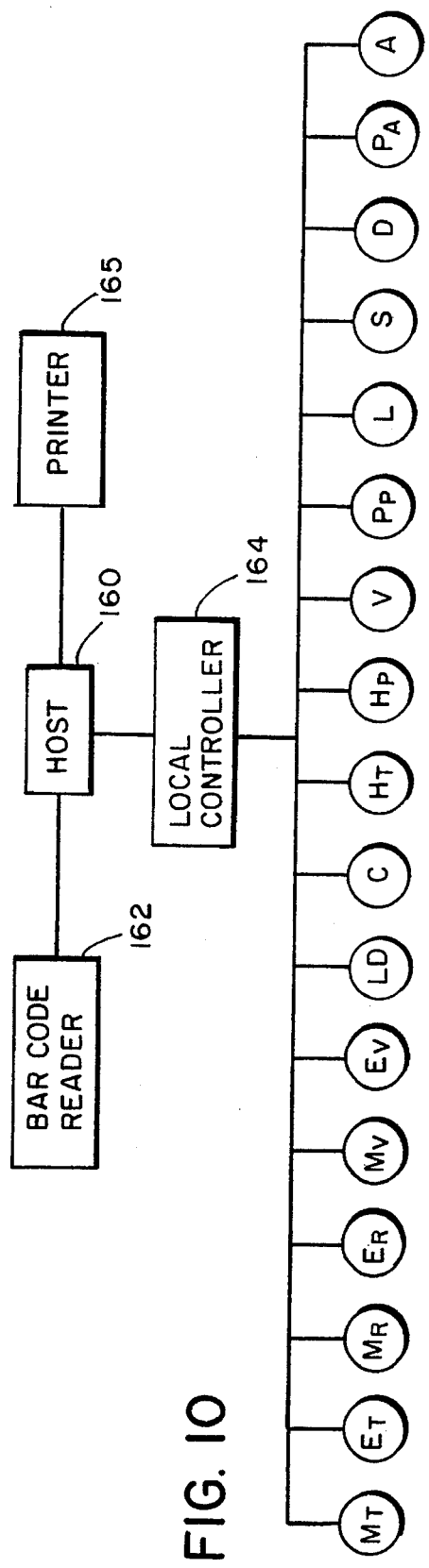
FIG. 10 is an electrical block diagram of the system.

An electrical block diagram of the system is illustrated in FIG. 10. The system includes a host computer and terminal 160 which receives user inputs, provides user prompts, indicates assays to be performed, and provides printed reports. The host computer is coupled to a bar code reader 162. Both the sample containers and reagent containers may have bar code labels thereon for identifying the patient and reagent, respectively. The bar code input into the system minimizes clerical errors.

Figures 11A, 11B:
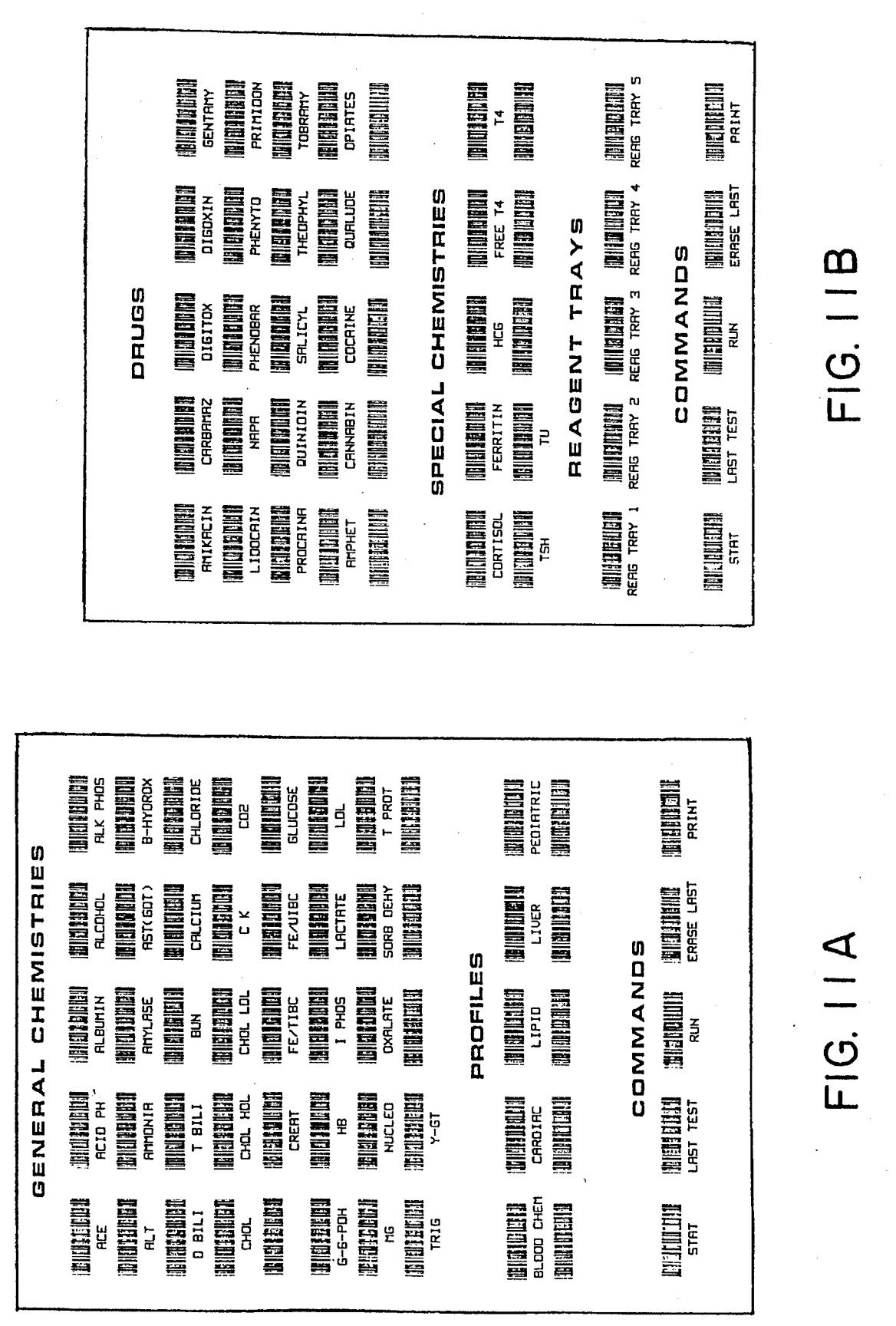

FIGS. 11A and 11B illustrate two sides of a single sheet which may be used to indicate to the system particular assays which are to be performed with respect to particular patient samples. It can be seen that lists of general chemistries, drugs and special chemistries which can be detected by the analyzer are listed in human-readable form. A bar code identifying each such assay is associated with each. Each of the profiles identifies with a single input a plurality of assays to be performed. After the operator has scanned the patient identifier label on the sample container to identify the sample to the system, he may determine from the patient's chart the particular analyses to be performed and then indicate the analyses to the system by scanning bar codes of the sheet of FIGS. 11A and 11B.

In addition to identifying assays, the optically encoded sheet may indicate which of several trays is positioned in the analyzer. The reagent trays may be loaded beforehand with particular reagents which are identified to the computer system. The bar code input may be used to indicate to the system which reagent tray is on the turntable. Finally, specific commands may be provided to the system using the bar code input.

The bar code input results in less error and is more efficient than inputting directly into the processor either by keyboard or cursor.

The printer 165 of the system is of a quality which permits the host to generate a sheet of adhesive labels, each of which identifies the source of samples in both human readable form and machine-readable bar code.

In the applications where the instrument is used as a clinical chemistry analyzer, one or more labels for patient identification can go to the clipboard at the patient's bed or other convenient location, so that the label can be attached to any work orders for the patient and any specimen drawn from the patient, to be later read by the analyzer. Provision is made through keyboard for optional patient demographics, such as name, doctor, identification numbers and test results.

Further provision is made through keyboard entry or through RS232 communications port for demographics as well as test results from other instruments, so that they can be logged onto the same report form.

Thus, providing hardware and software system that handles patient demographics, archiving of prior patient results, generation of bar code labels coded to patient identification, reading of those labels as part of the setup of the test requirements for each sample, reading of the sheets indicating which tests are to be run and what operations to be performed, automatically providing location for insertion of appropriate reagents and test samples, running the chemical assays in a self-calibrating system, and reporting the results either by RS232 output or by printing a hard copy or by displaying on a graphics terminal alphanumerically or graphically, or any combination of these as required by the operator, increases throughput, minimizes errors and extra hardware.

A local controller 164 is provided to respond to the instructions from the host computer 160 and control operation of the many elements of the system while collecting data from various sensors. Specifically, the controller drives the turntable stepper motor $M_T$, the arm rotating stepper motor $M_R$ and the and the arm vertical drive stepper motor $M_V$ related encoders $E_T$, $E_R$ and $E_V$. As illustrated in FIG. 2, drivers to the motor coils may be shared in a multiplexed fashion. Each of several stepper motors which, for example, drive the turntable and arm and various pumps includes four coils 166. The coils are coupled to four drivers 168 each of which is coupled to a coil of each motor. A specific motor to be driven at any instant is selected by a number of motor drivers 170, each of which draws current through a common node of all coils in a motor. Thus, for example, five motors can be driven with only nine drivers in a multiplexed fashion; whereas 20 drivers would be required if an individual set of four drivers were provided for each coil.

The controller 164 also monitors a level detector LD which is preferably a simple capacitor detector with the metal probe 30 serving as one plate of the capacitor. As the probe contacts the liquid in a sample container, reagent container or test cell, the capacitance changes abruptly. That signal indicates the fluid level so that the available volume of liquid can be monitored and the probe need not be dipped deep into the liquid. Also, at the wash station, the signal provides a reference for moving the probe down into the seal of the injection station and can verify that wash solution is in the wash station.

The controller also controls the Peltier cooler, the turntable heater and the probe heater C, $H_T$ and Hp and responds to associated sensors. It drives the probe pumps Pp and associated valve V. It controls the electrical voltage applied to the lamp L of the optical analyzer and the shutter S. It further receives data from the detector array D. Also, it controls the pump PA associated with the flow-through analyzer and controls and receives data from the analyzer A.

Among the capabilities programmed into the host 160 is the ability to control the voltage level applied to the analyzer lamp 1 in order to extend the life of the lamp. To obtain low frequency light of about 340 nanometers, a halogen-filled quartz lamp is used. The lamp must be run very hot to obtain the 340 nanometer light, and that heat leads to a shorter life. The life of the lamp can be substantially increased by reducing the voltage input where the low wavelength signals are not required for a particular sequence of assays.

The host 160 also supports automatic multiple point calibration of the system. With standard samples positioned at predetermined locations in the tray, a series of calibration tests may be run by the system, and the host uses the results of those tests to plot a calibration curve. The system can then automatically provide calibrated outputs from the tests. Further, if a test provides an output which is above the highest calibrated level of the system, the system may automatically dilute the sample, or reduce the optical input in time or intensity, to bring the output within the calibration range and take into account the dilution or reduction in input when reporting the results of an analysis. Also, the system may respond to specific user instructions to dilute the sample. This is particularly advantageous where the user knows the sample is too concentrated, but eliminates the potential for user error in diluting the sample. It is also useful where only a limited amount of the sample is available. Dilution allows for a greater number of assays even though those assays may be performed at the lower end of the calibration curve.

Figure 13A:
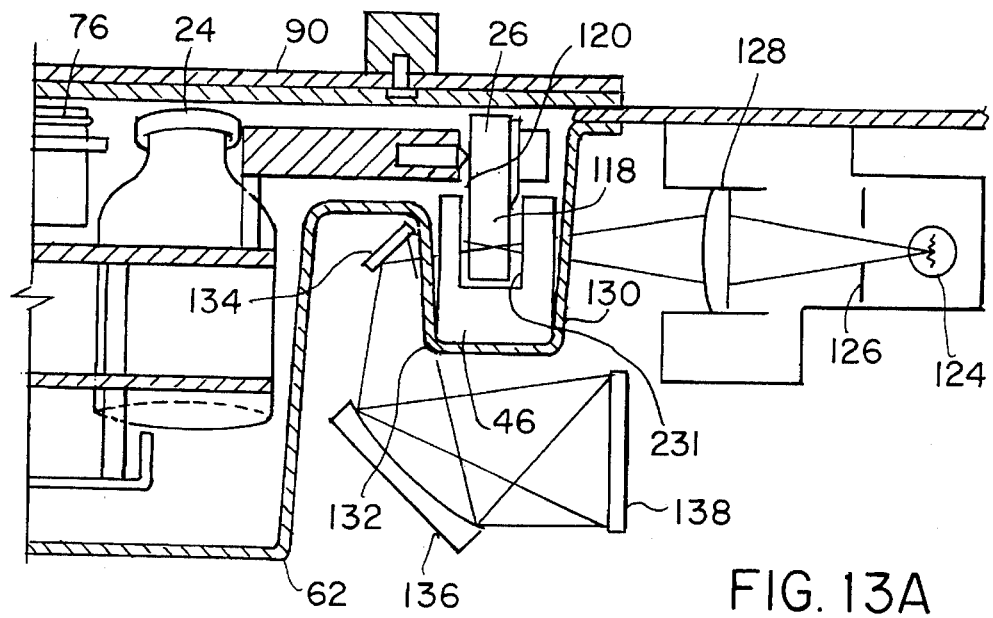
FIG. 13A is a partial cross sectional view of an alternative heater configuration supporting the test cell segments.

An alternative embodiment of the analyzer provides a turntable and related components of FIG. 1 and FIG. 2A with a modified heater 46 providing a channel in heater 231, as shown in FIG. 13A. By this alternative embodiment, it becomes unnecessary for turntable 20, FIG. 1 to support segments 26, as the latter may be caused to slide in the channel by rotation of the turntable.

Figure 12:
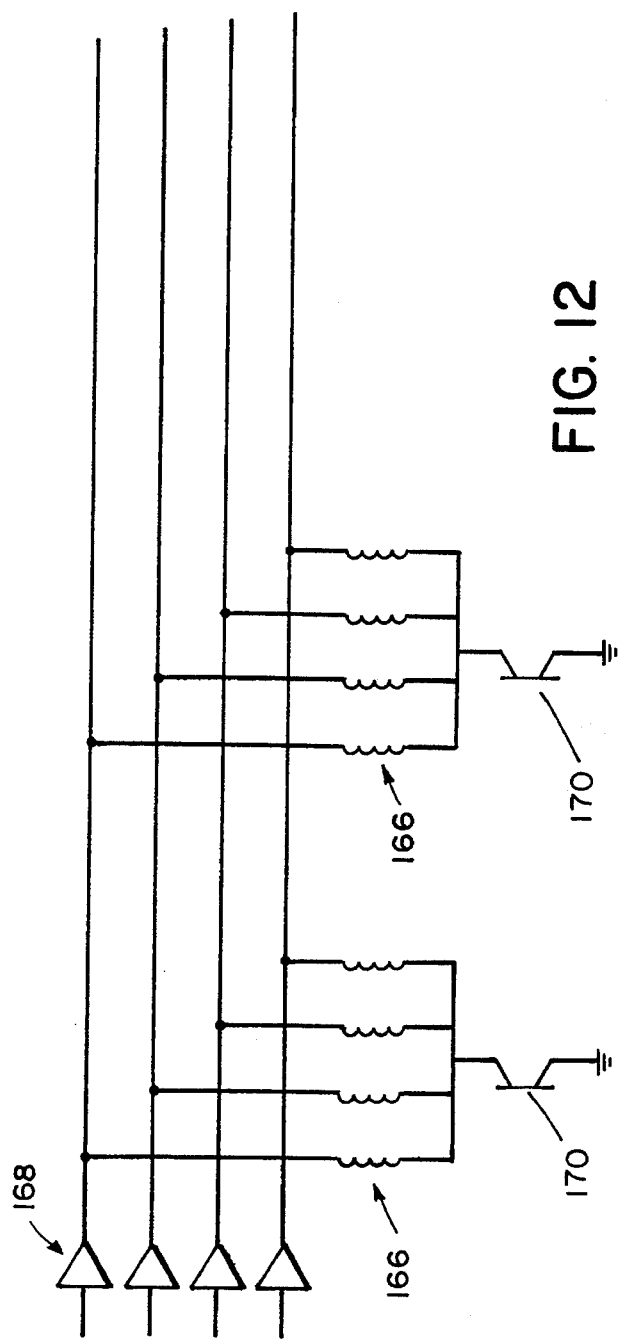
FIG. 12 is an illustration of a motor drive circuit used in the system of FIG. 1.
Figure 13B:
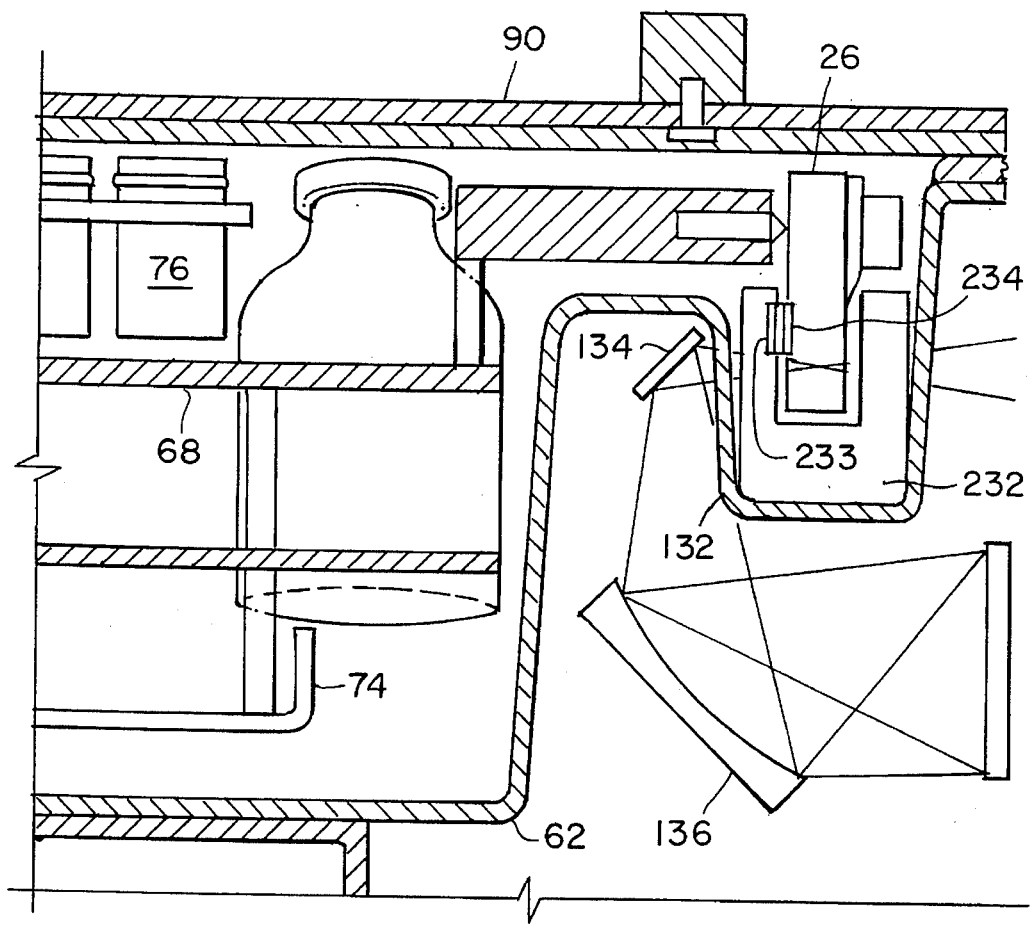
FIG. 13B is a partial cross sectional view of yet another arrangement for supporting and driving the test cell segments.

Yet another alternative embodiment of the analyzer may also provide for independent movement of the segments relative to the remainder of the turntable, so that segment position is independent of sample and reagent position. One possible embodiment of this alternative is indicated in FIG. 13B, wherein heater 232 is provided with groove 233 in the inner wall of the channel holding in position toothed belt 234, which is driven by a motor or the like, so that certain of the teeth engage appropriately with the segments to move them under the control of controller 164 of FIG. 12. This independence of segment position from that of the sample and reagent containers increases the throughput of the analyzer, as the sample and reagent containers and the segments can each be placed optimally for sample and reagent pickup and dispensing by the probe.

An alternative embodiment of segment 26 of FIG. 6 is to provide 16 or more individual test cells in each segment to increase the walkaway capacity of the analyzer.

The software directing the operation of the controller can provide increased analyzer throughput by causing pump 50, FIG. 4 to aspirate larger volumes of a reagent than is required for a single assay when more than one of the same assay is to be performed.

This procedure, for example, may cause pump 50 to pick up sufficient reagent from one reagent bottle 24, FIG. 1 for ten or more assays and then to pick up sample for one assay. Pumps 48 and/or 50 dispense the sample and an adequate amount of reagent into the first reaction cup. A second sample is subsequently picked up and dispensed with another adequate amount of reagent into the second reaction cup without returning to the reagent bottle, and this process is continued until some ten samples and aliquots of the reagent have been dispensed. Thus, throughput is greatly increased by the elimination of movement to and from the reagent bottle 9 out of the 10 times.

In another example of the bulk handling of reagent, a sufficient amount of reagent is drawn into the probe from one reagent bottle for a number of assays. The individual aliquots of reagent are then delivered to the test cells independent of delivery of the samples. Either before or after delivery of the reagent, aliquots of sample are individually drawn and dispensed. This approach allows for dispensing of pumping fluid with the sample into the test cell as a diluent. Typical pumping fluids include water, saline and water with surfactant. The approach also allows for photoanalysis of blank aliquots of reagent before the samples are dispensed.

The two bulk methods of delivering reagent may also be used in combination. For example, one reagent may be drawn in bulk and delivered to multiple test cells for blank readings, and a second reagent may then be drawn into the probe in bulk and then dispensed to individual test cells with individual aliquots of sample.

The design of washer/injector station, FIG. 9, provides a volume of basin 142 which does not drain quickly into outlet 148. This volume, which is filled with wash liquid from overflow of center well 140, provides a place for the temporary immersion of probe 30 to wash both outside and inside of the probe while pumps 48 and/or 50 are moved to expel sample, or reagent, or pumping solution, or all three. This immersion of the probe during initial was eliminates the atomization of potentially infectious or hazardous solutions which could occur during dispensing of solutions into the air over the washer station.

A further benefit of this feature is that this volume of fluid in the basin provides a prewash of the probe. When the probe is introduced into the center well, the probe causes less contamination of the wash solution in the center well. The probe is cleaner as the result of the double wash, and the flow rate of the wash solution may be reduced, conserving this solution and reducing operating cost of the analyzer.

Since a lamp has a predictable stabilization time period, it is frequently possible to predict when the lamp's voltage can be reduced or turned off completely when it is not needed for a reading. Included in the preferred embodiment of the analyzer is time-dependent control of lamp 124 of FIG. 2A. By reducing the voltage applied to the lamp when intervals between measurements occur—such as waiting for slow endpoint chemistries, or delays while tests are being set up—the life of the lamp can be extended greatly, reducing service time and expenses.

Additional life extensions may be achieved, when longer delays occur, by utilizing the lamp control circuit to completely turn off its voltage automatically until its warm-up time requires turn-on of the lamp, so that its light output will be stable when measurements of samples are to be made. Thus, the whole instrument can be left on to maintain temperature control of critical areas without the lamps being on and its life shortened.

While this invention has been particularly shown and described with references to preferred embodiments thereof, it will be understood by those skilled in the art that various changes in form and details may be made therein without departing from the spirit and scope of the invention as defined by the appended claims. For example, the system described allows for only absorption-type tests using the test cells. Fluorescent-type tests using optical filter wheels and with the detector at right angles to the incoming light are also readily implemented.

What is claimed is:

1. A method of dispensing reagent and samples from containers into test cells in an automatic analyzer system comprising the steps of:

drawing into a probe from a reagent container an amount of reagent sufficient for plural tests; and subsequently drawing sample into the probe and dispensing sample and reagent for plural tests by sequentially, for each test, drawing into the probe sample for an individual test and dispensing sample and reagent for the individual test without drawing additional reagent between tests.

2. A method of dispensing reagent and samples from containers into test cells in an automatic analyzer system comprising the steps of:
   a) drawing a sample probe pumping solution from a reservoir into pumps for priming said pumps;
   b) drawing into a probe from a reagent container an amount of reagent sufficient for plural tests;
   c) dispensing aliquots of reagent into individual test cells for plural tests; and
   d) drawing into the probe individual aliquots of sample and dispensing the aliquots of sample with aliquots of sample probe pumping solution into the individual test cells wherein steps b and c occur prior to step d.

* * * * *